(12) United States Patent  
Kaste et al.

(10) Patent No.: US 6,699,712 B2
(45) Date of Patent: Mar. 2, 2004

(54) ELECTROPORATION CHAMBER

(75) Inventors: Keith Kaste, El Cerrito, CA (US);
John Morrill, Alameda, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 39 days.

(21) Appl. No.: 10/105,037

(22) Filed: Mar. 20, 2002

(65) Prior Publication Data

US 2003/0180939 A1 Sep. 25, 2003

(51) Int. Cl.[7] .................................................. C12M 1/42
(52) U.S. Cl. .................. 435/285.2; 435/809; 204/228.2; 204/297.14; 204/600
(58) Field of Search ........................... 435/285.2, 173.6, 435/461, 470, 809; 204/600, 297.1, 297.14, 228.8

(56) References Cited

U.S. PATENT DOCUMENTS 5,422,272 A * 6/1995 Papp et al. ............... 435/285.2
6,150,148 A * 11/2000 Nanda et al. ............. 435/173.6

FOREIGN PATENT DOCUMENTS

| DE | 3501865 A | * | 7/1986 | ............ A01H/1/00 |
| JP | 63049069 A | * | 3/1988 | ............ C12M/1/00 |
| JP | 63230071 A | * | 9/1988 | ............ C12M/1/00 |
| JP | 01240180 A | * | 9/1989 | ............ C12M/1/00 |
| JP | 03133373 A | * | 6/1991 | ............ C12M/1/00 |
| JP | 03280874 A | * | 12/1991 | ............ C12M/1/42 |

* cited by examiner

Primary Examiner—William H. Beisner
(74) Attorney, Agent, or Firm—M. Henry Heines; Townsend and Townsend and Crew

(57) ABSTRACT

A shocking chamber for performing electroporation is constructed in the form of a base and a hinged lid which when lowered forms an enclosure with the base that fully encloses a cuvette and impresses a high voltage across the cuvette, the voltage connection becoming disengaged upon the simple raising of the lid. The base contains two pairs of electrical leads, one pair engaging the cuvette with spring-loaded contacts that provide electrical connections to the cuvette while helping to secure the cuvette in place, and the other pair joined to high-voltage terminals. A shunt built into the lid bridges the two pairs of leads in the base when the lid is closed and pivots out of the way to clear all leads when the lid is opened. These and other features of the construction provide the user with a safe and secure means of forming the high-voltage electrical connections used in electroporation in an apparatus that can be operated with one hand.

6 Claims, 4 Drawing Sheets

ELECTROPORATION CHAMBER

BACKGROUND OF THE INVENTION

1. Field of the Invention

This invention resides in the field of laboratory apparatus for electroporation. In particular, this invention concerns the construction of the shocking chamber in which biological cells suspended in the appropriate media are exposed to the high-voltage electrical pulses that are used in electroporation.

2. Description of the Prior Art

Electroporation, also known as transfection, is a process by which a biological cell is exposed to a high-voltage electric potential to create transitory pores in the cell membrane that re-close when the potential is removed. The pores allow large molecules such as nucleic acids and proteins to enter the cell from the cell suspension medium, and electroporation is therefore a means of infusing the cells with these molecules. Electroporation is particularly useful in placing foreign DNA inside living cells, thereby enabling the cells to express desirable proteins or to otherwise behave in a specified manner dictated by the infused DNA.

The amount of voltage used in electroporation depends on the cell type and the species being infused. Smaller cells, for example, tend to require higher field strengths, as do larger molecules, and voltages can range from as low as 200 V/cm to as high as 35,000 V/cm. With voltages of this magnitude, user safety is a concern.

An electroporation apparatus typically includes a cuvette to hold the cell suspension and a shocking chamber in which the cuvette is inserted and the voltage applied. The cuvette is generally inserted into the chamber by way of a slide. This requires two hands and entails a certain degree of awkwardness and hence risk on the part of the user.

SUMMARY OF THE INVENTION

The present invention resides in a shocking chamber which includes a base and a hinged lid, the chamber designed to receive and fully enclose a cuvette and containing electric circuitry arranged to impose high voltage across the cuvette once the cuvette is inserted in the chamber, the circuitry further arranged to engage a high-voltage power source upon simple closing of the lid and to disengage the power source upon opening of the lid, both of which can be done by a simple one-hand operation. The base contains two pairs of electrical leads, one pair engaging the cuvette with spring-loaded contacts that both provide electrical connections to the cuvette and secure the cuvette to the base of the chamber, and the other pair joined to high-voltage terminals on the chamber exterior. The engagement and disengagement of the power source to the cuvette is achieved by a shunt built into the lid. The shunt bridges the two pairs of leads in the base when the lid is closed and pivots out of the way to clear all leads when the lid is opened. In preferred embodiments of the invention, each of the four electric leads in the base has a hook-shaped end extending upward toward the lid so that the shunt contacts engage the hooks for a secure connection. In further preferred embodiments, the chamber contains electrically insulating partitions separating each of the electrical leads to avoid arcing and inadvertent finger contact by, and injury to, the user.

Further features, advantages, and preferred embodiments of the invention will be apparent from the description that follows.

DETAILED DESCRIPTION OF THE INVENTION AND PREFERRED EMBODIMENTS

While this invention is susceptible to considerable variation in structural details such as the arrangement and shapes of the parts and their dimensions, the invention will be best understood by a detailed explanation of one particular embodiment. The drawings attached hereto depict such an embodiment.

Figure 1:
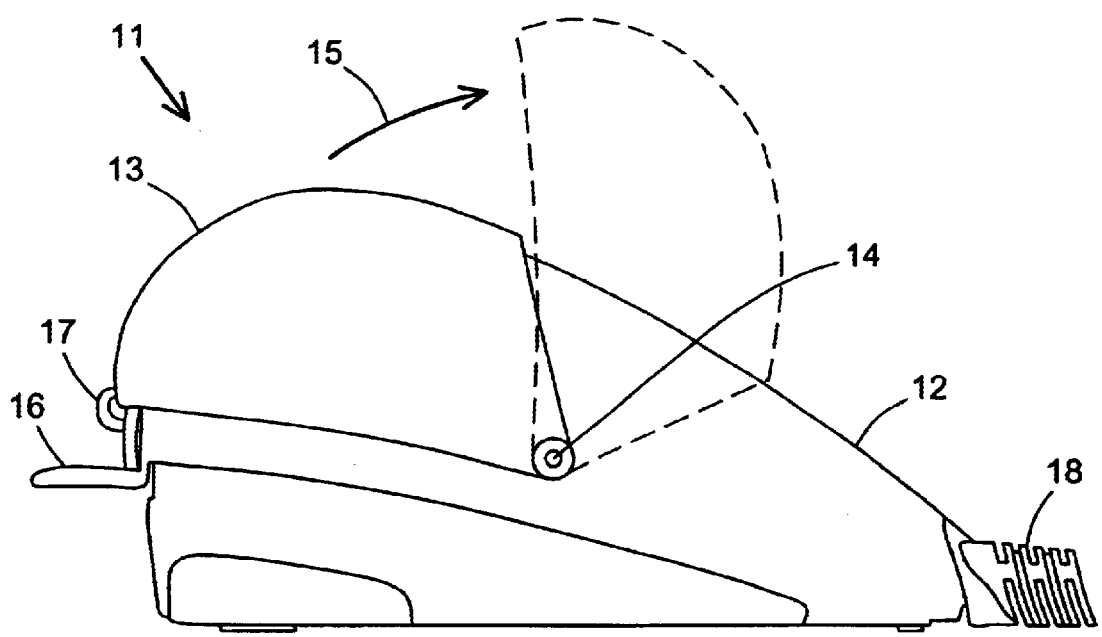
FIG. 1 is a side elevation of a shocking chamber in accordance with the present invention.

FIG. 1 is a side view of an electroporation chamber 11 of this embodiment, having a base 12 and a lid 13 which is mounted to the base through a hinge connection 14. The lid is shown in the closed position but is rotatable in the direction of the arrow 15 around the hinge connection 14 to an open position shown in dashed lines. A thumb-operated closure tab 16 is positioned at the front end of the chamber. The tab 16 is part of the base, and the pressing of the tab with one's thumb results in release of the lid from a catch 17, the lid being spring-loaded to open spontaneously upon release. Extending from the rear of the base of the chamber is a strain-relief support 18 for a high-voltage cable. Power supplies for electroporation systems are described in the literature and commercially available, and although none were originally intended for use in chambers designed in accordance with the present invention, they can indeed be used with the chamber shown in these Figures. Examples of power supplies are described by Ragsdale, U.S. Pat. No. 4,750,100, issued Jun. 7, 1988; Calvin, U.S. Pat. No. 5,098,843, issued Mar. 24, 1992; Uhen, U.S. Pat. No. 6,103,084, issued Aug. 15, 2000; and Ragsdale, U.S. Pat. No. 6,258,592, issued Jun. 10, 2001. The disclosures of each of these patents are incorporated herein by reference in their entirety.

Figure 2:
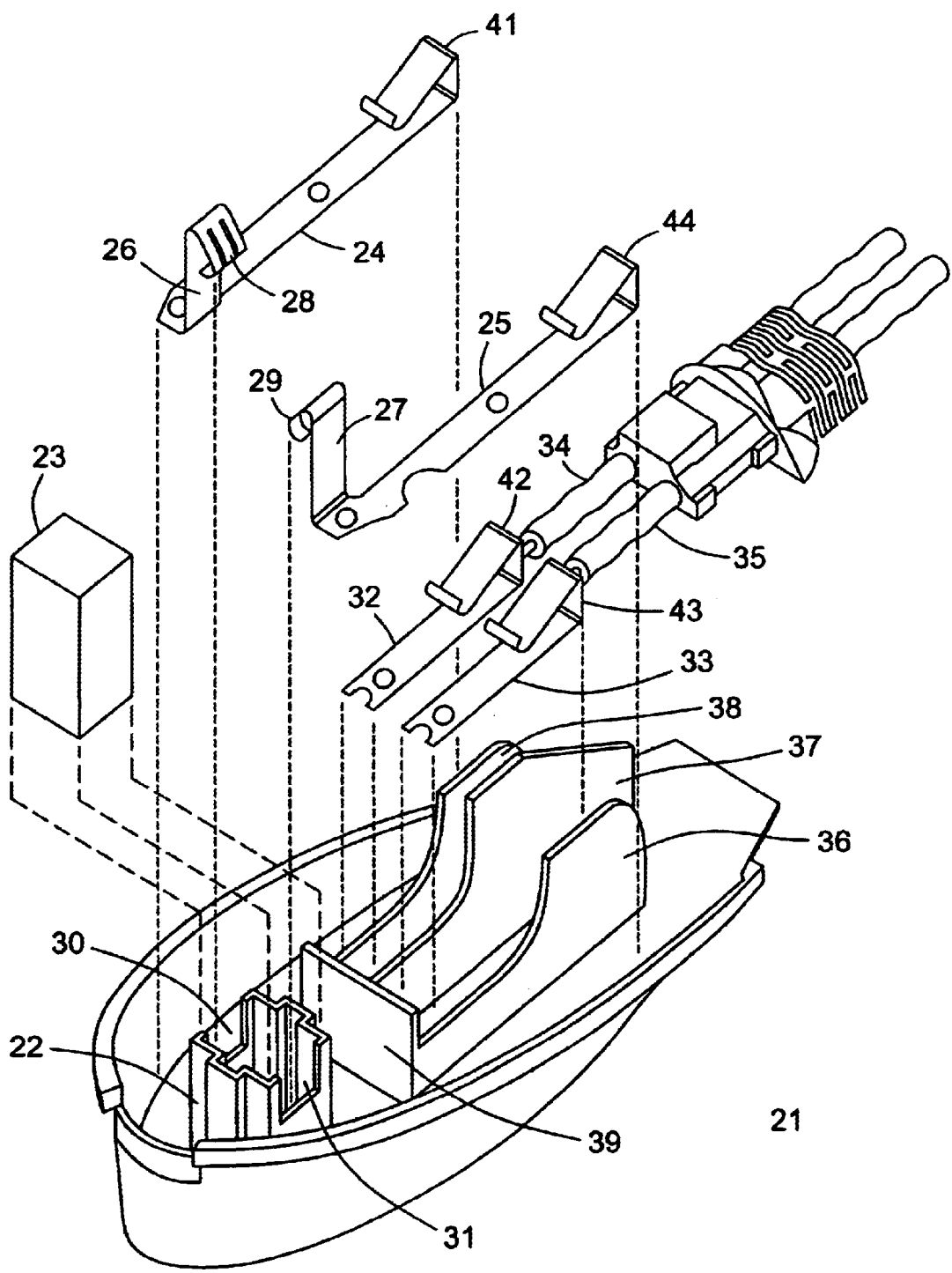
FIG. 2 is an exploded perspective view of a portion of the base component of the shocking chamber of FIG. 1.

The interior components of the base 12 are shown in a perspective view in FIG. 2 with the electric leads elevated above for clarity. A platform 21 forms the floor of the base, and extending upward from the platform toward the front end (i.e., the end at the lower left of the figure, which is the end at which the lid opens to permit access to the user) is an open-top enclosure 22 sized to receive a standard electroporation cuvette 23, which is shown poised above the platform ready for insertion. A pair of electric leads 24, 25, also shown in an elevated position above the platform, are secured to the platform adjacent to the outer edges of the platform. The forward ends 26, 27 of these leads are shaped to provide electrical contact with the cuvette walls when the cuvette is inserted. Each of these forward ends 26, 27 is turned upward at approximately a 90-degree angle and then inward at an acute angle. These angled ends 28, 29 protrude into the cuvette enclosure 22 through notches 30, 31 in the enclosure walls, causing the leads to press against the cuvette. The electric leads are formed of a resilent conductive material so that the angled ends 28, 29 function as springs pressing against the cuvette walls to hold the cuvette in place while also providing a strong electrical connection to the cuvette.

A second pair of electric leads 32, 33, also shown in an elevated position above the platform, are positioned between the electric leads of the first pair. Power is supplied to these leads through high-voltage cables 34, 35. There is no electrical connection on the platform 21 or within the base as a whole between the leads of the first pair 24, 25 and those of the second pair 32, 33, and electrically insulating partitions 36, 37, 38 separate each of the four leads to provide further protection against arcing as well as inadvertent finger contact by the user. An end partition 39 further isolates the high-voltage leads 32, 33 from the cuvette. The four leads are thus in a parallel arrangement in this embodiment, with the high-voltage supply leads 32, 33 in the center and the two cuvette-contacting leads 24, 25 on either side of the supply leads. Alternative arrangements can be devised that will function in the same or an equivalent manner, such as reversing the positions of the two sets of leads, using circular or arc-shaped leads rather than elongated linear leads, or any configuration that will still allow for isolation of the leads and safe handling.

Various structural elements that will typically be included have been omitted from FIG. 2 so that the elements described above can be readily shown and identified. These additional elements may include elements used for assembling the floor to the remaining portions of the base, elements used for stabilizing the leads against distortion that might result from resistance heating, and elements used for covering portions of the leads that are not used as sites for electrical contact. Other such elements will be readily apparent to engineers skilled in the design and construction of electrical equipment.

Connection and disconnection between the two sets of electric leads for purposes of supplying high voltage to the cuvette is achieved at the rear ends of each of the four leads. Shown in the exploded view of FIG. 2, these rear ends 41, 42, 43, 44 when mounted to the floor of the base are aligned in a row toward the rear of the floor. Each is bent upward at a right angle, then forward at an acute angle with a forward edge curved upward to result in a hook-shaped profile. Like the forward ends 28, 29 of the two cuvette-contacting leads, these hook-shaped rear contacts act as springs to press against contacts in the shunt (described below). The springs in this case press downward against the shunt contacts since the shunt contacts enter the openings of the hooks underneath the upwardly curved forward edges of the hooks.

Figure 3:
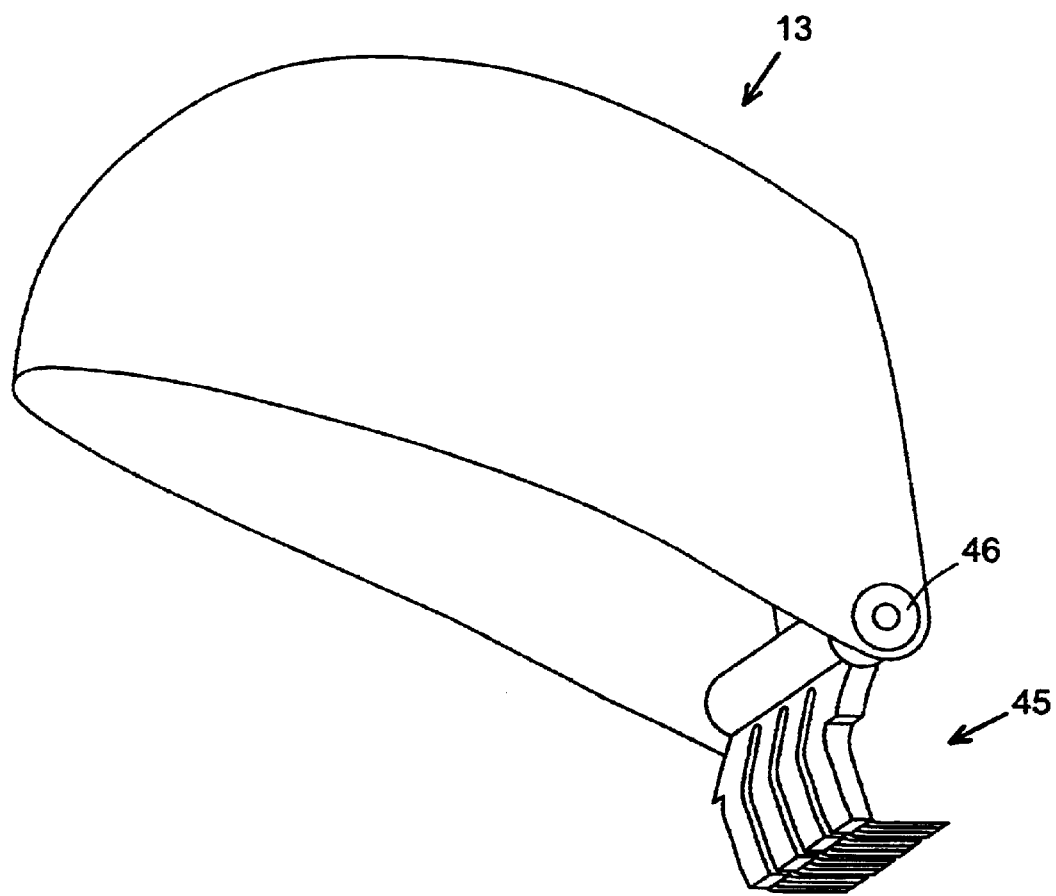
FIG. 3 is a perspective view of the lid component of the shocking chamber of FIG. 1.
Figure 4:
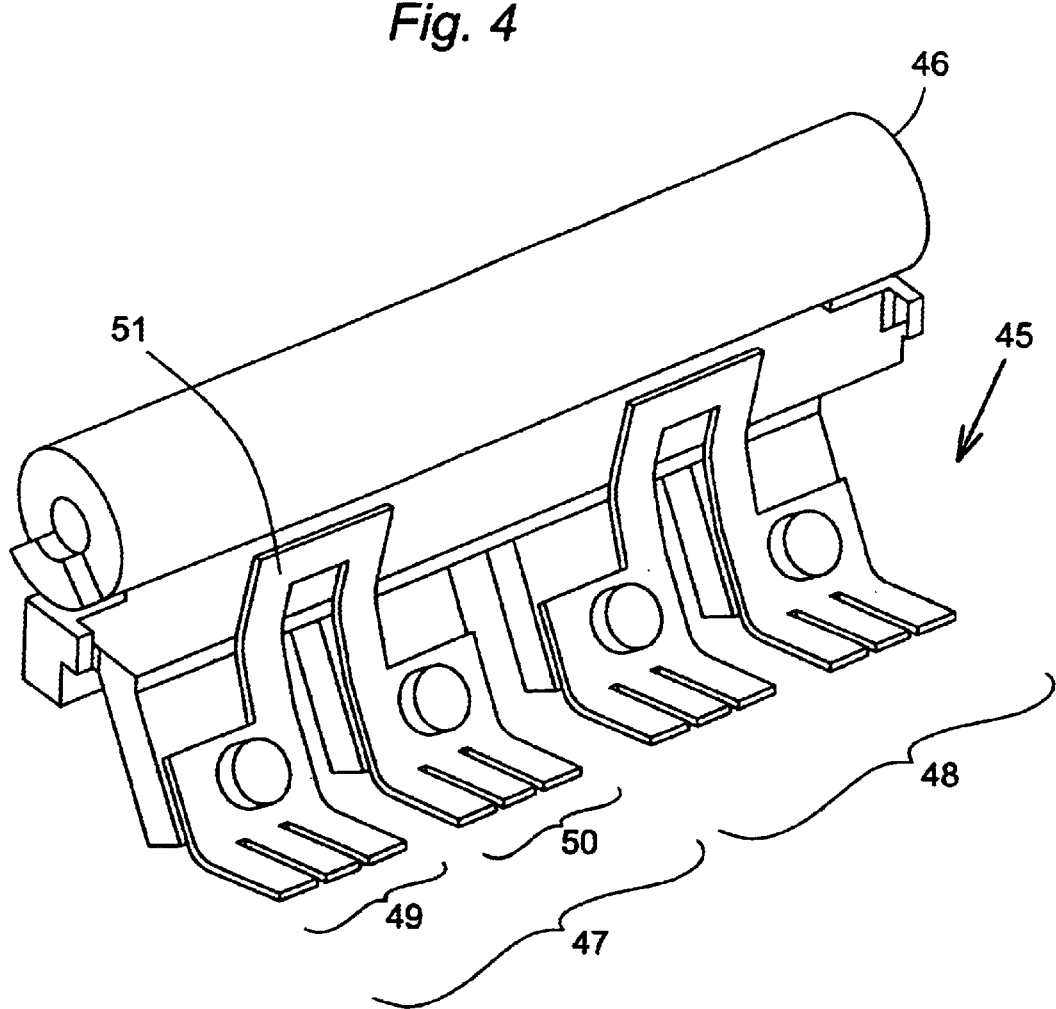
FIG. 4 is a perspective view of the shunt affixed to the lid component of FIG. 3.

The shunt 45 is shown in the perspective views of FIGS. 3 and 4. FIG. 3 shows the entire lid 13 with the shunt 45 extending from the hinge 46 that joins the lid to the base. FIG. 4 is a rear view of the hinge 46 and shunt 45, showing the two halves 47, 48 of the shunt. The two halves are separated by a gap which electrically insulates one from the other. The two halves are identical, each consisting of a pair of feet 49, 50 joined by a connecting bridge 51, the feet and bridge being of conductive material and bolted to the hinge which is electrically insulating. All four feet are aligned in a row and bent at an angle that will cause them to enter the openings of the contact hooks 41, 42, 43, 44 in the base and press upward against the undersides of the hooks. The shunt 45 is rigidly secured to the hinge 46 such that the shunt feet rotate into engagement with the contact hooks when the lid is closed and rotate out of engagement when the lid is opened.

For the shunt as for the electric leads in the base, alternative arrangements can be made which serve the same or an equivalent function. The shunt feet may for example press downward on the hooks rather than upward; the shunt feet may themselves be configured to provide a spring-loaded effect rather than the leads in the base; and the arrangement of the shunt feet may be non-linear rather than linear.

The foregoing description is offered primarily for purposes of illustration. Still further variations, substitutions, and embodiments that fall within the novel concepts of the invention will be readily apparent to those skilled in the art.

What is claimed is:

1. A chamber for receiving a cuvette containing biological cells and biological molecules and for exposing said cuvette to an electric field to effect entry of said molecules into said cells by electroporation, said chamber comprising:

a housing comprising a base and a lid hinge-mounted to said base;

a cuvette holder affixed to said base;

first and second pairs of electrical leads affixed to said base, each lead of said first pair terminating at a forward end in a spring-loaded forward contact, said forward contacts oriented to jointly grasp and electrically engage a cuvette in said cuvette holder, and said second pair supplied by a high-voltage source, with no electrical connection in said base between said leads of said first pair and said leads of said second pair; and a shunt affixed to said lid and arranged thereon such that opening and closing said lid causes said shunt to pivot between (a) an engagement position when said lid is closed, in which said shunt bridges said first pair of electrical leads to said second pair and thereby forms a high-voltage connection from said second pair through said first pair to said forward contacts of said first pair, and (b) a non-engagement position when said lid is open, in which said first and second pairs are not in electrical contact and said forward contacts are electrically isolated from said high-voltage connection.

2. A chamber in accordance with claim 1 in which said leads of said first and second pairs terminate in spring-loaded rear contacts that engage said shunt when said shunt is in said engagement position.

3. A chamber in accordance with claim 1 in which said first and second pairs of electrical leads are parallel strips of electrically conductive material.

4. A chamber in accordance with claim 1 further comprising electrically insulating partitions separating all of said electrical leads from each other.

5. A chamber in accordance with claim 1 in which said rear ends of said first and second pairs of electrical leads each have hook-shaped profiles with openings, and said shunt comprises four feet, each one arranged to enter one of said openings and press against said hook to form an electrical connection.

6. A chamber in accordance with claim 1 further comprising a thumb-operated closure for securing said lid to and releasing said lid from said base.

* * * * *